United States Patent [19]

Sato et al.

[11] Patent Number: 5,414,160
[45] Date of Patent: May 9, 1995

[54] METHOD FOR DIMERIZING BUTENES, DIMERIC COMPOSITION OF BUTENES AND METHOD FOR PRODUCING ALCOHOLS BY MEANS THEREOF

[75] Inventors: Keiichi Sato, Tokyo; Yuuji Kawaragi; Yasuko Higashino, both of Yokohama, all of Japan

[73] Assignee: Mitsubishi Kasei Corporation, Tokyo, Japan

[21] Appl. No.: 244,718

[22] PCT Filed: Oct. 14, 1993

[86] PCT No.: PCT/JP93/01477

§ 371 Date: Jun. 16, 1994

§ 102(e) Date: Jun. 16, 1994

[87] PCT Pub. No.: WO94/08924

PCT Pub. Date: Apr. 28, 1994

[30] Foreign Application Priority Data

Oct. 16, 1992 [JP] Japan .................. 4-278986

[51] Int. Cl.6 .............. C07C 29/141; C07C 31/125; C07C 11/02; C07C 2/30
[52] U.S. Cl. ..................... 568/883; 524/296; 560/76; 585/16; 585/513
[58] Field of Search ............. 568/883; 585/513, 16

[56] References Cited

U.S. PATENT DOCUMENTS

| | | |
|---|---|---|
| 2,625,527 | 1/1953 | Smith et al. ............... 568/883 |
| 2,728,798 | 12/1955 | Russum et al. ............. 568/883 |
| 2,792,417 | 5/1957 | Desa ........................ 568/883 |
| 3,255,259 | 6/1966 | Mertzweiller et al. ........ 568/883 |
| 3,513,218 | 5/1970 | Faltings et al. . |
| 3,636,034 | 1/1972 | Ohsumi et al. .............. 568/883 |
| 3,709,953 | 1/1973 | Bergem et al. . |
| 4,155,946 | 5/1979 | Sato et al. . |
| 4,476,341 | 10/1984 | Mathys . |
| 4,855,527 | 8/1989 | Page et al. . |
| 4,870,038 | 9/1989 | Page et al. . |
| 5,026,933 | 6/1991 | Blain et al. . |
| 5,196,624 | 3/1993 | Threlkel et al. . |

FOREIGN PATENT DOCUMENTS

| | | |
|---|---|---|
| 0569032 | 11/1993 | European Pat. Off. . |
| 57-167932 | 10/1982 | Japan . |
| 57-169433 | 10/1982 | Japan . |
| 61-15849 | 4/1986 | Japan . |
| 160928 | 6/1989 | Japan .................. 568/883 |
| 789777 | 1/1958 | United Kingdom . |

*Primary Examiner*—Joseph E. Evans
*Attorney, Agent, or Firm*—Oblon, Spivak, McClelland, Maier & Neustadt

[57] ABSTRACT

A method for dimerizing an n-butene wherein a catalyst system is used which is produced in situ from an organonickel compound having no nickel-halogen bond, a triarylphosphine and/or a monoalkyldiarylphosphine, an organoaluminum compound and hydrogen. The resulting octenes are excellent as a raw material of alcohols for a plasticizer, and an excellent plasticizer can be obtained from alcohols having 9 carbon atoms produced by using the octenes.

18 Claims, No Drawings

METHOD FOR DIMERIZING BUTENES, DIMERIC COMPOSITION OF BUTENES AND METHOD FOR PRODUCING ALCOHOLS BY MEANS THEREOF

TECHNICAL FIELD

The present invention relates to a method for dimerizing butenes by means of a specific catalyst, a dimeric composition of butenes composed mainly of octenes produced by the dimerization reaction of butenes and a method for producing alcohols useful as a raw material of a plasticizer by means of the dimeric composition.

BACKGROUND ART

Extensive researches have been made heretofore on catalyst systems for uniformly dimerizing lower monoolefins such as ethylene, propylene and butene. As the catalysts, Ziegler catalysts having transition metals as central catalyst components are usually advantageous in terms of selectivity to dimers of lower monoolefins. In particular, when a catalyst obtained from a mixture of a nickel compound and an organoaluminum halide compound is used, good results have been obtained with respect to both dimerization activity and selectivity. Further, with respect to dimerization of butenes, a catalyst system consisting of a nickel compound selected from the group consisting of a nickel salt of a higher mono- or di-carboxylic acid having from 5 to 20 carbon atoms and a coordination complex of an organic phosphine and a nickel halide, an organoaluminum compound and hydrogen, has been proposed as a means for providing an improved yield of octenes, in Japanese Examined Patent Publication No. 42249/1991.

It is generally known that in these dimerization reactions of butenes, the resulting octenes are obtained not only as a mixture of various skeletal isomers such as n-octene, 3-methylheptene and 3,4-dimethylhexene but also as a mixture of various double-bond isomers as a result of isomerization reactions which occur competitively with the dimerization reactions. Further, it is already known that alcohols having 9 carbon atoms (hereinafter referred to as "INA") obtained by subjecting the octenes obtained in the above dimerization reaction to a hydroformylation reaction and a hydrogenation reaction are advantageously used as a raw material of a plasticizer for a vinyl chloride resin (U.S. Pat. No. 789,777 and Japanese Examined Patent Publication No. 15849/1986). Further it is known that INA is excellent alcohols for a plasticizer for a vinyl chloride resin in respect of heat resistance and cold temperature flexibility as compared with 2-ethylhexanol which is obtained by hydroformylation, dimerization and hydrogenation of propylene and which has been used commonly and extensively as an alcohol for a raw material of a plasticizer.

On the other hand, as a method for producing octenes other than dimerization of butenes, there is an oligomerization reaction of olefins. For example, Japanese Unexamined Publication No. 132534/1989 discloses a method for oligomerizing olefins having from 2 to 10 carbon atoms by means of a zeolite catalyst surface-treated with a trialkylpyridine compound or an organic phosphorus compound.

As described above, the octenes obtained by dimerization of butenes have linear and various branched structures and are obtained as a mixture of many isomers having double bonds at different positions.

When these products are used, for example, as starting materials of the hydroformylation reaction described above, octenes having high degrees of branching will remain in the system as unreacted substances since in general, octenes having lower degrees of branching are more reactive in the hydroformylation reaction. Further, when INA produced by hydroformylation and hydrogenation reactions of octenes is used as a raw material of a plasticizer, INA having a low degree of branching has an advantage of providing a product excellent in important properties of a vinyl chloride resin such as cold resistance and resistance to volatilization.

However, in a dimerization reaction of butenes, a reaction substrate usually contains a large amount of internal olefins such as 2-butene and it is quite difficult to obtain octenes having low degrees of branching economically in a high yield from such a reaction substrate that contains a large amount of internal olefins. With respect to the above-mentioned catalyst system for dimerizing n-butenes proposed in Japanese Examined Publication No. 42249/1991, the resulting octene mixture is not very suitable for industrial use, in particular, for use in the field of plasticizer as described above, because of the high production ratio of 3,4-dimethylhexene having a high degree of branching. The above-mentioned method for producing INA proposed in U.S. Pat. No. 789,777 and Japanese Examined Patent Publication No. 15849/1986 is not necessarily satisfactory in this respect.

Further, the method for oligomerizing olefins proposed in Japanese Unexamined Patent Publication No. 132534/1989 is not necessarily satisfactory as a method for producing octenes economically and selectively, when it is taken into consideration that the fractional distillation process of the product obtained as a mixture of olefins having a wide range of number of carbon atoms is complex and that the selectivity to octenes in the product is not necessarily sufficient.

Accordingly, objects of the present invention are to develop a catalyst system capable of improving the yield of octenes and the selectivity to octenes having low degrees of branching in dimerization of butenes and to develop a method by which INA having a low degree of branching can be produced selectively in a high yield.

DISCLOSURE OF INVENTION

The present inventors have conducted extensive studies to achieve the above objects in production of octenes and in production of INA. As a result, they have found that when a specific dimerization catalyst is used in dimerization of butenes, it is possible to selectively produce octenes within a specific range in a high yield and that when the octenes within a specific range are used in production of INA, it is possible to remarkably improved the performance of a plasticizer and have accomplished the present invention on the basis of such discoveries.

Namely, the method for dimerizing of the butenes of the present invention is characterized in that in a method for dimerizing butenes in the presence of a catalyst, a catalyst system is used which is produced in situ from (i) an organonickel compound having no nickel-halogen bond, (ii) a triarylphosphine and/or a monoalkyldiarylphosphine, (iii) an organoaluminum compound and (iv) hydrogen. The dimeric composition of butenes of the present invention is a high-molecular weight product obtained by dimerization of butenes and is characterized in that the content of octenes is at least 70% by weight, the total of the contents of normal octene, monomethylheptene and dimethylhexene in the octenes is at least 90% by weight, the content of highly-branched forms which are branched not less than dimethylhexene in the octenes is at most 15% by weight and the average degree of branching of the octenes is from 0.85 to 1.15. Further, the method for producing alcohols of the present invention is characterized in that the dimeric composition or the octenes obtained by the dimerization method is subjected to a hydroformylation reaction and a hydrogenation reaction.

Now, the present invention will be described in detail.

As the butenes to be used in the present invention, not only single substances of 1-butene and 2-butene, but also a mixture thereof or a butene fraction having a high n-butene content which is obtained by separating butadiene and isobutene from a $C_4$ fraction (BB fraction) obtained by pyrolysis of a hydrocarbon oil such as naphtha, may be used preferably. A BB fraction obtained by catalytic cracking (such as FCC) of a hydrocarbon oil such as the heavy oil, is a mixture composed mainly of butene and butane, and a butene fraction having a high n-butene content which is obtained by separating isobutene from such BB fraction by distillation, may also be used preferably.

In a dimerization reaction of these butenes, by the use of the specific catalyst system according to the present invention, octenes having quite low degrees of branching can be produced with high activity. Here, the degree of branching represents the number of groups such as methyl groups or ethyl groups, branched from a main hydrocarbon chain. For example, the degrees of branching of n-octene, 3-methylheptene and 3,4-dimethyhexene are 0, 1 and 2, respectively. An average degree of branching of octenes is the average of degrees of branching of octene components (n-octene, 3-methylheptene, 3,4-dimethylhexene and the like) in an octene mixture. For example, in the case of an octene mixture containing the same amounts of 3-methylheptene and 3,4-dimethylhexene, the average degree of branching is 1.5.

The dimerization reaction catalyst to be used in the present invention is a catalyst system produced in situ from (i) an organonickel compound having no nickel-halogen bond, (ii) a triarylphosphine and/or a monoalkyldiarylphosphine, (iii) an organoaluminum compound and (iv) hydrogen.

The organonickel compound having no nickel-halogen bond to be used in the present invention may, for example, be various organic nickel salts, specifically, carboxylic acid salts of nickel such as nickel formate, nickel trifluoroacetate, nickel oxalate, nickel acetate, nickel octanoate, nickel dodecanoate, nickel naphthenate, nickel oleate and nickel benzoate. It is preferred to dehydrate these carboxylic acid salts before use, and preferably a carboxylic acid salt having from 1 to 18 carbon atoms, more preferably a carboxylic acid salt having from 1 to 8 carbon atoms, further preferably a carboxylic acid salt having from 1 to 4 carbon atoms is used. Other preferred examples include complex compounds having no inorganic radical such as bis-(acetylacetonato)nickel, bis(hexafluoroacetylacetonato)nickel and bis(cyclooctadiene)-nickel, and particularly preferred is an acetylacetonate complex compound.

When a nickel-phosphine complex compound in which a halogen is directly bonded to nickel is used as the organonickel compound, the dimerization activity or the selectivity for desired octenes may be reduced. For example, when the organic nickel salt is the one of which ligand phosphine is an alkyl phosphine or cycloalkylphosphine such as $NiCl_2(PEt_3)_2$ and $NiCl_2(PCy_3)_2$ (wherein Et is an ethyl group and Cy is a cyclohexyl group), the dimerization reaction proceeds well. However, the resulting octenes tend to show a product distribution with high degrees of branching. On the other hand, when an organonickel halide complex compound having coordinated arylphosphines to be used in the present invention, such as $NiCl_2(PPh_3)_2$ (wherein Ph is a phenyl group), is used, the resulting octenes show a product distribution with low degrees of branching like the case of the catalyst system of the present invention. However, the dimerization activity is reduced.

In this case, a factor of the low activity is low solubility of a nickel complex, and such a nickel halide complex as described above in which a triarylphosphine (a soft phosphine) such as $PPh_3$ is coordinated, is generally less soluble in a solvent and in butenes which are the reaction substrate, as compared with a nickel halide complex in which a trialkylphosphine (a hard phosphine) such as $PEt_3$ and $PCy_3$ is coordinated or a combination form of a nickel compound in which no halogen is directly bonded to nickel and a phosphine to be used in the present invention. Therefore, it is assumed that decrease in the amount of active catalyst components which contribute to the dimerization reaction results in reduction in the reactivity.

As the organoaluminum compound, for example, the following compounds may be used. Namely, as a trialkylaluminum compound of the general formula $AlR_3$ (wherein R is an alkyl group having from 1 to 5 carbon atoms), trimethylaluminum, triethylaluminum, tri-n-propylaluminum, tri-n-butylaluminum, tri-i-propylaluminum, tri-i-butylaluminum and tri-t-butylaluminum may, for example, be mentioned. Otherwise, as a monohalogenodialkylaluminum, dihalogenomonoalkylaluminum or sesquihalogenoalkylaluminum compound of the general formula $AlR_2X$, $AlRX_2$ or $Al_2R_3X_3$ (wherein R is an alkyl group having from 1 to 5 carbon atoms and X is a halogen atom), diethylaluminum monochloride, ethylaluminum dichloride, ethylaluminum sesquichloride, propylaluminum dichloride and isobutylaluminum dichloride may, for example, be mentioned. Further, an organic aluminoxane compound which is obtained by partial hydrolysis of such a trialkylaluminum compound or a halogenoalkylaluminum compound as described above may be mentioned.

Among these organoaluminum compounds, an alkylaluminum halide compound is preferred. Particularly, a dihalogenomonoalkylaluminum compound such as ethylaluminum dichloride is more preferred.

In the method of the present invention, by the use of a catalyst system produced in situ from an organonickel compound having no nickel-halogen bond, an organoaluminum compound, hydrogen and a triarylphosphine or a monoalkyldiarylphosphine, an octene mixture having a low degree of branching can be obtained in a high yield. By using such an octene mixture as a starting material, the reaction activity of hydroformylation is increased and the degree of branching of a resulting alcohol mixture (INA) obtained via hydroformylation and hydrogenation reactions can be lowered.

If constituting components of the catalyst include no phosphine compound to be used in the present invention or if another phosphine compound such as a trialkylphosphine and a tricyclohexylphosphine is used, the degrees of branching of the resulting octenes are not satisfactory and the performance, as a plasticizer, of INA produced by using such octenes as a raw material, is not necessarily satisfactory. The performance as a plasticizer should be evaluated comprehensively based on e.g. ① plasticizing efficiency, ② volatile weight loss (heat resistance), ③ cold temperature flexibility, ④ extractability by kerosene (oil resistance) and ⑤ electrical resistance (insulating properties) and is not a matter of only single property such as heat resistance. The INA obtained by the method of the present invention provides an excellent performance as a plasticizer even from the comprehensive viewpoint.

As the triarylphosphine to be used in the present invention, a compound of the general formula $PAr_3$(-wherein Ar is a phenyl group or naphthyl group which may have a substituent and the substituent is a hydrocarbon group such as an alkyl group having from 1 to 6 carbon atoms, an aryl group and a cycloalkyl group, an alkoxy group or a halogen atom such as Cl, Br and F), may, for example, be used. Specifically, triphenylphosphine, tris(p-chlorophenyl)phosphine, tris(p-fluorophenyl)phosphine, tris(m-chlorophenyl)phosphine, tris(p-methoxyphenyl)phosphine, tris(o-methoxyphenyl)phosphine, tris(p-biphenylyl)phosphine, tri-m-tolylphosphine, tri-p-tolylphosphine, tri-o-tolylphosphine, tris(p-isopropylphenyl)phosphine, tris(2,4,6-trimethylphenyl)phosphine, tris(3,5-dimethylphenyl)phosphine, tri-1-naphthylphosphine, p-tolyldiphenylphosphine, m-tolyldiphenylphosphine, di-p-tolylphenylphosphine, o-tolyldiphenylphosphine, 2-biphenylyldiphenylphosphine, 1-naphthyldiphenylphosphine and 2-naphthyldiphenylphosphine may, for example, be mentioned. Among them, triphenylphosphine and tris(p-substituted phenyl)phosphines are used preferably.

As the monoalkyldiarylphosphine to be used in the present invention, a compound of the general formula $PRAr_2$ (wherein Ar is a phenyl group or a naphthyl group which may have a substituent, preferably a phenyl group, the substituent is, for example, a hydrocarbon group such as an alkyl group having from 1 to 6 carbon atoms, an aryl group and a cycloalkyl group, an alkoxy group or a halogen atom such as Cl, Br and F, preferably an alkyl group having from 1 to 6 carbon atoms, and R is an alkyl group having from 1 to 8 carbon atoms), may, for example, be used. Specifically, n-propyldiphenylphosphine, i-propyldiphenylphosphine, n-butyldiphenylphosphine, n-octyldiphenylphosphine and di-p-tolyl-n-butylphosphine may, for example, be mentioned.

In the method of the present invention, hydrogen is used as the fourth catalyst component. Although its action is not clear, it is assumed to provide various functions such as removal of impurities in the reaction system (for example, reaction-inhibiting substances such as conjugated dienes), promotion of producing catalytically active species, and contritrition to a stability of the catalyst. In any case, the activity of the dimerization reaction is distinctly increased by the presence of hydrogen. There is no particular restriction to the amount of hydrogen to be used, and it may be used in an amount which brings about a result desirable for the catalytic activities. It is, in terms of a partial pressure of hydrogen, usually from 0.01 to 50 $kg/cm^2$, preferably from 0.1 to 20 $kg/cm^2$.

In order to form the catalyst system, in the dimerization reaction of butenes conducted in the present invention, the above-mentioned catalyst components, i.e. an organonickel compound having no nickel-halogen bond, a triarylphosphine and/or a monoalkyldiarylphosphine compound, an organoaluminum compound and hydrogen, may be mixed with one another in any order. However, it is preferred to preliminarily mix an organonickel compound having no nickel-halogen bond and a triarylphosphine or monoalkyldiarylphosphine compound or form them into a complex thereof before use. It is also preferred to contact such a Ni—P compound and an organoaluminum compound simultaneously in the presence of butenes in order to obtain octenes having low degrees of branching in a high yield.

In the method of the present invention, although the use of a solvent for reaction is not essential, a solvent inert to the reaction, for example, an aromatic hydrocarbon such as benzene, toluene, xylene or dodecylbenzene, an aliphatic hydrocarbon such as hexane, heptane or cyclohexane, or a halogenated aromatic hydrocarbon such as chlorobenzene may be used.

In the dimerization reaction, the concentration of the nickel component in the liquid phase is usually from $10^{-2}$ to $10^2$ mmol/l. The molar ratios of the respective catalytic components affect the dimerization activity and the product distribution. In the present invention, the molar ratio of the organoaluminum compound to the nickel compound in the catalyst is usually within a range of from 2 to 100, preferably from 5 to 50. The molar ratio of the above-mentioned triarylphosphine or monoalkyldiarylphosphine compound to the organonickel compound is from 0.05 to 20, preferably from 0.5 to 5.

If the molar ratio of the organoaluminum compound to the organonickel compound in the catalyst is too small, the reaction with oxygen or water and the like present in a trace amount during the dimerization reaction causes a drastic decrease in the catalytic activity. On the other hand, if the dimerization reaction is conducted under such a condition that the ratio is larger than required, there will be no remarkable improvement of the dimerization activity, and such is not economically advantageous. If the molar ratio of the phosphine compound to the organonickel compound is too small, the dimerization activity will decrease and the resulting octenes will have larger degrees of branching. On the contrary, if the ratio is too large, the dimerization activity may decrease although it also depends upon the amount of the organoaluminum compound, and such is not economically advantageous.

With respect to the conditions for the dimerization reaction to be conducted in the present invention, the reaction temperature is usually from −10° to 100° C., preferably from 0° to 80° C., more preferably from 10 to 80° C. It is determined properly depending on the productivity of the process, the stabilities of the organonickel compound and the organoaluminum compound used, etc.

It is effective to let the catalyst components be present sufficiently in the liquid phase of butenes, and the reaction pressure is preferably at a level of from 2 to 30 kg/cm². The dimerization method of the present invention can be conducted even while a paraffinic hydrocarbon such as methane, ethane, propane or butane, or an inert gas such as nitrogen, argon or carbon dioxide is contained in the starting materials of the reaction. The dimerization reaction may be conducted in a continuous system or a batch system.

In the dimerization method of the present invention, the reaction conditions, in particular the concentration of the catalyst, the reaction temperature and the reaction time (the contacting time) largely affect the product selectivity. In general, if the reaction conditions are raised, the reaction activity will be improved, but the reactivity for trimerization or higher oligomerization will also increase, whereby the selectivity for the desired octenes will decrease, in particular the content of the normal form and the monomethyl form will decrease.

By the dimerization reaction conducted in the present invention, it is possible to obtain octenes which are excellent especially as a raw material of INA for a plasticizer, selectively in a high yield. Particularly, the octenes produced in the present invention contain little skeletal isomer involving C—C bond cleavage, which is usually produced when a dimerization reaction is conducted by means of a solid phosphoric acid catalyst or a catalyst having Ni supported on an inorganic porous carrier such as $SiO_2$ and $Al_2O_3$, and the total of the contents of normal octene, monomethylheptene and dimethylhexene is at least 90% by weight. Moreover, the content of highly-branched products which are branched not less than dimethylhexene of a 2-branched type is at most 15% by weight, and an octene composition with the average degree of branching of octenes defined above being at most 1.15, is provided. Further, the octene content in the product obtained by the dimerization reaction is at least 70% by weight. Here, the high-molecular weight product represents a compound having a molecular weight of 400 or less which is generally produced in an oligomerization reaction of butenes.

When such octenes having low degrees of branching are used in, for example, a process for producing aldehydes which are precursors of alcohols for a plasticizer, i.e. a hydroformylation reaction, the reaction can be pushed to a higher conversion than when conventional octene compositions are used, and thus they are preferred also from the economical aspect. Further, when the octenes are led to alcohols via a hydroformylation reaction and a hydrogenation reaction, the plasticizer produced therefrom will have improved plasticizer performance with respect to e.g. cold resistance, brittleness and volatility, as compared with a plasticizer derived from a conventional octene composition and thus is of great value in industrial use.

In the dimeric composition of butenes composed mainly of octenes which produces preferable results as described above, the content of octenes in the high-molecular weight product obtained by the dimerization reaction is at least 70% by weight, preferably at least 80% by weight, more preferably at least 90% by weight, and as to the skeletal structure of the produced octenes, the total of the contents of normal octene, monomethylheptene and dimethylhexene is at least 90% by weight, preferably 95% by weight, more preferably 99% by weight, the content of highly-branched forms which are branched not less than dimethylhexene therein is at most 15% by weight, preferably at most 10% by weight, more preferably at most 7% by weight, further preferably at most 5% by weight, and the average degree of branching of the produced octenes as defined above is from 0.85 to 1.15, preferably from 0.85 to 1.10, more preferably from 0.85 to 1.00, further preferably from 0.90 to 0.95.

Next, a method for producing alcohols having 9 carbon atoms by using octenes obtained in the above-mentioned dimerization reaction of butenes, as a starting material, will be described in detail.

In the method of the present invention, usually, octenes obtained in the above-mentioned dimerization reaction of butenes are firstly rectified at atmospheric pressure or reduced pressure to separate high-boiling components, etc. which are contained in small amounts, and then the octene fraction obtained by the rectification is subjected to a hydroformylation reaction with carbon monoxide and hydrogen to produce aldehydes having 9 carbon atoms.

The above hydroformylation reaction is conducted by a conventional method. The reaction conditions of the hydroformylation are not particularly critical and either a conventional rhodium method or cobalt method, may be used.

As a rhodium source in the case of the rhodium method, an organic salt such as $Rh(OAc)_3$, an inorganic salt such as $Rh(NO_3)_3$ or $RhCl_3$, or a complex such as $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$ or $[RhCl(COD)]_2$ (wherein Ac is an acetyl group, acac is an acetylacetonato, and COD is cyclooctadiene, respectively), may be used.

As a cobalt source in the case of the cobalt method, in addition to an organic salt such as cobalt laurate and an inorganic salt such as $Co(NO_3)_2$, a complex such as $Co_2(CO)_8$ and $CoH(CO)_4$ may be used.

The conditions employed, may be such that the reaction pressure is usually from atmospheric pressure to 300 kg/cm²G, the reaction temperature is usually from 50° C. to 150° C., the $H_2/CO$ ratio is usually from 1 to 10 by molar ratio and the catalyst concentration is usually from 0.1 to 1000 ppm in terms of Rh atoms. As a ligand, an organic phosphorus compound such as triphenylphosphine or triphenylphosphite, or an oxide thereof may suitably be used usually at a molar ratio of from 1 to 1000 to the above catalyst.

There is no need to use a solvent for reaction. However, if necessary, a solvent inert to the reaction, for example, an aromatic hydrocarbon such as benzene, toluene, xylene or dodecylbenzene, an aliphatic hydrocarbon such as hexane, heptane or cyclohexane, an ether such as dibutyl ether, ethylene glycol dimethyl ether, triethylene glycol dimethyl ether or tetrahydrofuran, or a ester such as diethyl phthalate or dioctyl phthalate may be used. Also, the aldehydes or alcohols produced during the hydroformylation reaction may be used as a solvent. High-boiling by-products such as polycondensates of aldehydes may be also used. The reaction may be conducted in a continuous system or a batch system.

In the above hydroformylation reaction, the structures of the resulting aldehydes largely differ depending not only on the effect of the ligand, but also on the central metal of the catalyst used. Namely, in general, a rhodium catalyst has a much greater hydroformylation activity as compared with a cobalt catalyst, but branched aldehydes are likely to be produced due to its strong internal isomerizing ability. Whereas, the above-mentioned octenes used in the present invention have low degrees of branching and thus have advantages that even if the hydroformylation reaction is conducted by a rhodium method, the alcohols finally obtained will have relatively low degrees of branching, and that the hydroformylation activity will increase.

Then, alcohols having 9 carbon atoms are produced by a hydrogenation reaction of the resulting aldehydes, which may be conducted by a conventional method. Namely, it is conducted by using a conventional hydrogenation catalyst such as Ni, Cr or Cu under a reaction pressure usually of from atmospheric pressure to 150 kg/cm$^2$G at a reaction temperature usually of from 40° C. to 300° C. And then, by a conventional rectification, alcohols having 9 carbon atoms (i.e. INA) can be obtained.

The INA thus obtained can be made into a plasticizer (such as a phthalate plasticizer) by esterifying it with an acid such as phthalic anhydride or adipic acid by a conventional method, followed by purification, and the resulting plasticizer has an excellent performance.

BEST MODE FOR CARRYING OUT THE INVENTION

Now, the specific embodiments of the present invention will be described in further detail with reference to Examples. However, it should be understood that the present invention is by no means restricted by such specific Examples, as long as it does not exceed its gist.

Examples 1 to 5 and Comparative Examples 1 to 8

Into a micro autoclave made of stainless steel with a 70 ml internal volume, which had been evacuated and flushed with nitrogen, 0.024 mmol of a nickel compound and 0.072 mmol of a phosphine compound as shown in Table 1 and 3 ml of m-xylene were introduced, and then a heptane solution containing 0.3 mmol of dichloroethylaluminum was introduced thereto under a nitrogen atmosphere, provided that in Comparative Example 5, Comparative Example 6 and Comparative Example 7, 0.024 mmol of a NiCl$_2$(PPh$_3$)$_2$ complex, a NiCl$_2$(PEt$_3$)$_2$ complex and a NiCl$_2$(PCy$_3$)$_2$ complex are used, respectively, instead of the nickel compound and the phosphine compound.

Then, after introducing 20 ml of trans-2-butene, hydrogen gas was injected until total pressure reached 5 kg/cm$^2$G, the micro autoclave was sealed, and then the reaction was conducted at 40° C. for 5 hours while stirring. After completion of the reaction, the micro autoclave was cooled to room temperature. After purging the unreactive gas, 2 ml of methanol was added to terminate the reaction. After the reaction solution containing mixed octenes was hydrogenated to the corresponding octanes, the concentrations of the products were analyzed by a gas chromatography analysis method (column: Shimadzu Corp. CBP1 capillary 0.25 $\phi \times 50$ m and 10% SE-30/Chromosorb 2 m). The results are shown in Table 1.

Example 6

A dimerization reaction of trans-2-butene was conducted in the same manner as in Example 1 except that the amount of the phosphine compound used was changed to 0.036 mmol. The results are shown in Table 1.

TABLE 1

|  | Nickel salt | Phosphine compound | Yield of mixed octenes (%) | Skeletal distribution of octenes (%) | | | Average degree of branching |
|---|---|---|---|---|---|---|---|
|  |  |  |  | N | M | DM |  |
| Example 1 | Nickel acetate | PPh$_3$ | 71 | 14 | 79 | 7 | 0.93 |
| Example 2 | Nickel acetate | P(p-Cl—Ph)$_3$ | 65 | 13 | 79 | 8 | 0.95 |
| Example 3 | Nickel acetate | P(p-Me—Ph)$_3$ | 65 | 14 | 78 | 8 | 0.94 |
| Comparative Example 1 | Nickel acetate | — | 9 | 9 | 62 | 29 | 1.20 |
| Comparative Example 2 | Nickel acetate | PEt$_3$ | 67 | 5 | 72 | 23 | 1.18 |
| Comparative Example 3 | Nickel acetate | PCy$_3$ | 74 | 3 | 67 | 30 | 1.27 |
| Example 4 | Nickel octanoate | PPh$_3$ | 63 | 14 | 78 | 8 | 0.94 |
| Example 5 | Ni(acac)$_2$ | PPh$_3$ | 70 | 14 | 79 | 7 | 0.93 |
| Comparative Example 4 | Nickel octanoate | — | 28 | 9 | 61 | 30 | 1.21 |
| Comparative Example 5 | NiCl$_2$(PPh$_3$)$_2$ | — | 14 | 16 | 76 | 8 | 0.92 |
| Comparative Example 6 | NiCl$_2$(PEt$_3$)$_2$ | — | 70 | 6 | 69 | 25 | 1.19 |
| Comparative Example 7 | NiCl$_2$(PCy$_3$)$_2$ | — | 72 | 3 | 67 | 30 | 1.27 |
| Comparative Example 8 | Nickel nitrate | PPh$_3$ | 18 | 14 | 71 | 15 | 1.01 |
| Example 6 | Nickel acetate | PPh$_3$ | 78 | 13 | 80 | 7 | 0.94 |

(Note)
N is n-octene, M is 3-methylheptene, and DM is 3,4-dimethylhexene.
The skeletal distribution of octenes is represented by weight percentage obtained by analysis after mixed octenes are hydrogenated to corresponding octanes.

Example 7

Into a 70 ml micro autoclave which had been evacuated and flushed with nitrogen, 11.2 g of trans-2-butene, 0.011 mmol of nickel acetate dissolved in hexane and m-xylene, 0.033 mmol of triphenylphosphine and 0.28 mmol of dichloroethylaluminum were introduced. The proportions of these compounds correspond to a molar ratio of the aluminum compound:the nickel compound of 25:1 and a ratio of nickel (metal):the olefin of 0.003:1 (g/mol).

Then, hydrogen gas was injected into the micro autoclave until the total pressure reached 3 kg/cm$^2$G, and the reaction was conducted at 42° C. for 5 hours while stirring. After completion of the reaction, the micro autoclave was cooled to room temperature. After the unreacted gas was purged, 2 ml of methanol was added to inactivate the catalyst system, and to terminate the reaction.

The reaction solution was analyzed by a gas chromatography analysis method (column: Shimadzu Corp. CBP1 capillary 0.25 mm$\phi \times$50 m and 10% SE-30/Chromosorb 2 m) to determine the concentrations of the products. The results are shown in Table 2.

Comparative Example 9

A dimerization reaction of trans-2-butene was conducted in the same manner as in Example 7 except that 0.011 mmol of bis(triethylphosphine)nickel chloride (Ni(PEt$_3$)$_2$Cl$_2$) was used instead of the nickel acetate and the triphenylphosphine. The results are shown in Table 2.

TABLE 2

| | Nickel compound and phosphorus compound | Yield of mixed octenes (%) | Skeletal distribution of octenes | | | Average degree of branching |
|---|---|---|---|---|---|---|
| | | | N | M | DM | |
| Example 7 | Nickel acetate + PPh$_3$ | 76 | 14 | 79 | 7 | 0.93 |
| Comparative Example 9 | Ni(PEt$_3$)$_2$Cl$_2$ | 75 | 5 | 72 | 23 | 1.18 |

(Note)
N is n-octene, M is 3-methylheptene, and DM is 3,4-dimethylhexene.
The skeletal distribution of octenes is represented by weight percentage obtained by analysis after mixed octenes are hydrogenated to corresponding octanes.

Example 8

(1) Synthesis of octenes 1.77 kg of trans-2-butene which had been sufficiently dehydrated with Molecular Sieve 13X and a n-heptane solution of ethylaluminum dichloride (25.45 mmol) were introduced into an induced stirring type autoclave made of SUS with an internal volume of 5 L under a nitrogen atmosphere. Then, while the autoclave was stirred, a xylene solution of nickel acetate (2.05 mmol) and a xylene solution of triphenylphosphine (6.15 mmol) which had been previously introduced into catalyst vessels connected to the autoclave were injected to the autoclave under hydrogen pressure to initiate the reaction, and then the reaction was conducted at 45° C. under a total pressure of 7.5 kg/cm$^2$G for 3 hours. After the reaction, the catalyst was inactivated by treatment with a 10% sulfuric acid aqueous solution, and then the organic phase was separated. After a part of the organic phase was subjected to a hydrogenation treatment by means of a 5% Pd/C catalyst, the skeletal structure of the octenes was analyzed by gas chromatography. The results are shown below.

n-octene 17%, 3-methylheptene 79%, 3,4-dimethylhexene 4%

Average degree of branching = 0.87

The selectivity of the resulting mixed octenes was 87.0% by weight.

The above operation was conducted twice.

(2) Collection of an octene fraction by distillation

The dimerization reaction solution which had been obtained in the above (1) was rectified in an oldershow type distillation column with an inner diameter 30 mm $\times$ 5 stages under atmospheric pressure, whereby an octene fraction at the temperature of from the temperature at the top of the column to 127° C. was obtained by separating low-boiling solvents, the high-boiling products and the catalyst components.

(3) Synthesis of INA

To an induced-stirring type autoclave made of SUS having an internal volume of 1 L, 600 ml of the octene fraction obtained in the above (2), 150 mg of Rh(acac)(CO)$_2$ and 4.65 g of a phosphite compound having the following structure were added under a nitrogen atmosphere, and then the reaction was conducted at 130° C. while the total pressure was maintained at 50 kg/cm$^2$G by an oxo gas of H$_2$/CO = 1. Five hours later, when gas absorption ceased, the reactor was cooled to room temperature, and the oxo gas was released. Then, the whole reaction solution was collected. Then, aldehydes and alcohols were collected by vacuum simple distillation under a pressure of 10 mmHg.

$$P\!\left[\!-\!O\!-\!\!\begin{array}{c}\text{aryl}\end{array}\!\!-\!+\right]_3$$

wherein +... a tertiary butyl group.

Then, to an induced type autoclave made of SUS with a 1 L internal volume, 600 ml of the liquid collected in the above simple distillation and 60 g of a nickel-chromium supported solid catalyst were introduced and reacted at the reaction temperature of 150° C. while the total pressure was maintained at 100 kg/cm$^2$G with hydrogen gas. Four hours later, when gas absorption ceased, the autoclave was cooled, and the hydrogen gas was released. Then, the whole reaction solution was taken out. After the solid catalyst was removed by filtration, the reaction solution was rectified by means of an oldershow type distillation column of inner diameter of 30 mm $\times$ 5 stages. The yield of INA through the hydrogenation reaction and the rectification was 95%.

(4) Synthesis of a plasticizer and its evaluation

The INA obtained in the above (3) and phthalic anhydride were esterified into a plasticizer by a conventional method. Then, the plasticizer and a vinyl chloride resin were mixed in a weight ratio of the plasticizer/the vinyl chloride resin of 67/100 to make them into a plasticized vinyl chloride resin by a conventional method, and various tests were conducted on it. The results are shown in Table 3.

Example 9

Synthesis and evaluation of a plasticizer were conducted in the same manner as in Example 8, except that in the synthesis of octenes of Example 8, instead of triphenylphosphine, the same amount of tri-m-tolylphosphine was used as the phosphine compound in the dimerization reaction catalyst. The results are shown in Table 3.

The results of analysis of the skeletal structures of octenes obtained in the above dimerization reaction are shown below.

n-octene 12.3%, 3-methylheptene 81.4%, 3,4-dimethylhexene 6.3%
  Average degree of branching=0.94
  Mixed octene selectivity=87.5% by weight

Example 10

Synthesis and evaluation of a plasticizer were conducted in the same manner as in Example 8, except that in the synthesis of octenes of Example 8, instead of triphenylphosphine, the same amount of o-tolyldiphenylphosphine was used as the phosphine compound in the dimerization reaction catalyst and the reaction time was 2 hours. The results are shown in Table 3.

The results of analysis of the skeletal structures of octenes obtained in the above dimerization reaction are shown below.

n-octene 16.0%, 3-methylheptene 79.0%, 3,4-dimethylhexene 5.0%
  Average degree of branching=0.89
  Mixed octene selectivity=89.3% by weight

Example 11

Synthesis and evaluation of a plasticizer were conducted in the same manner as in Example 8, except that in the synthesis of octenes of Example 8, instead of triphenylphosphine, the same amount of n-butyldiphenylphosphine was used as the phosphine compound in the dimerization reaction catalyst. The results are shown in Table 3.

The results of analysis of the skeletal structures of octenes obtained in the above dimerization reaction are shown below.

n-octene 9.4%, 3-methylheptene 80.9%, 3,4-dimethylhexene 9.7%
  Average degree of branching=1.00
  Mixed octene selectivity=83.0% by weight

Comparative Example 10

Synthesis and evaluation of a plasticizer were conducted in the same manner as in Example 8, except that in the synthesis of octenes of Example 8, the dimerization reaction was conducted at 45° C. for 5 hours by using a nickel acetate-ethylaluminum dichloridehydrogen catalyst system as a dimerization reaction catalyst without using a phosphine compound. The results are shown in Table 3.

The results of analysis of the skeletal structures of octenes obtained in the above dimerization reaction are shown below.

n-octene 9.0%, 3-methylheptene 60.7%, 3,4-dimethylhexene 30.2%
  Average degree of branching=1.21
  Mixed octene selectivity=96.2% by weight

Comparative Example 11

Synthesis and evaluation of a plasticizer were conducted in the same manner as in Example 8, except that in the synthesis of octenes of Example 8, instead of triphenylphosphine, the same amount of triethylphosphine was used as the phosphine compound in the dimerization reaction catalyst. The results are shown in Table 3.

The results of analysis of the skeletal structures of octenes obtained in the above dimerization reaction are shown below.

n-octene 4.9%, 3-methylheptene 72.1%, 3,4-dimethylhexene 23.1%
  Average degree of branching=1.18
  Mixed octene selectivity=93.4% by weight

Comparative Example 12

Synthesis and evaluation of a plasticizer were conducted in the same manner as in Example 8 except that an octene fraction obtained by dimerizing trans-2-butene in the presence of a $Ni/\gamma\text{-}Al_2O_3$ solid catalyst treated with ethylaluminum dichloride, was used. The results are shown in Table 3.

The results of analysis of the skeletal structures of octenes obtained in the above dimerization reaction are shown below.

Normal form 15%, monomethyl form 63%, dimethyl form 20%, trimethyl form 2%
  Average degree of branching=1.09
  Mixed octene selectivity=83.0% by weight

Example 12

To an induced stirring type autoclave made of SUS with a 1 L internal volume, 600 ml of octeries obtained in the above Example 8 and 3.48 g of $Co_2(CO)_8$ were added under a nitrogen atmosphere, and then reacted at 130° C. while the total pressure was maintained at 100 $kg/cm^2G$ with an oxo gas having a $H_2/CO$ molar ratio of 1. Eight hours later, when the gas absorption ceased, the reactor was cooled, a 3% NaOH aqueous solution was injected into it to inactivate the cobalt catalyst. Then, it was further cooled. After the oxo gas was released, the whole reaction solution was taken out and by liquid-liquid separation an organic phase was collected. Subsequently, aldehydes and alcohols were collected by vacuum simple distillation in the same manner as in Example 8, and then a hydrogenation reaction and rectification were conducted to collect INA. The INA was esterified with phthalic anhydride to obtain a plasticizer, and the performance of the plasticizer was evaluated. The results are shown in Table 3.

Comparative Examples 13 and 14

Synthesis and evaluation of plasticizers were conducted in the same manner as in Example 8 by using octenes obtained in Comparative Example 10 and Comparative Example 11. The results are shown in Table 3.

Comparative Example 15

Synthesis and evaluation of a plasticizer were conducted in the same manner as in Example 8 by using octenes obtained in Comparative Example 12. The results are shown in Table 3.

TABLE 3

| | Example 8 | Example 9 | Example 10 | Example 11 | Comparative Example 10 | Comparative Example 11 | Comparative Example 12 | Example 12 | Comparative Example 13 | Comparative Example 14 | Comparative Example 15 |
|---|---|---|---|---|---|---|---|---|---|---|---|
| Hydroformylation | Rhodium method | | | | | | | Cobalt method | | | |
| Plasticizing efficiency [100% modulus] $(kg/cm^2)$ | 73 | 73 | 72 | 74 | 79 | 78 | 78 | 74 | 77 | 76 | 76 |

TABLE 3-continued

|  | Example 8 | Example 9 | Example 10 | Example 11 | Comparative Example 10 | Comparative Example 11 | Comparative Example 12 | Example 12 | Comparative Example 13 | Comparative Example 14 | Comparative Example 15 |
|---|---|---|---|---|---|---|---|---|---|---|---|
| Volatile loss (%) [120 C. × 5 days] | 14.6 | 14.5 | 14.3 | 14.8 | 16.5 | 16.3 | 15.6 | 13.3 | 14.9 | 14.8 | 14.4 |
| Cold flex temperature (°C.) | −37 | −37 | −37 | −36 | −33 | −33 | −34 | −40 | −37 | −37 | −38 |
| Kerosene extraction (%) [room temp. × 1 day] | 42.1 | 42.0 | 42.0 | 41.0 | 40.0 | 40.0 | 40.6 | 43.7 | 41.8 | 41.9 | 42.4 |
| Electrical resistance [× $10^{13}$ Ω · cm] | 2.3 | 2.7 | 2.4 | 2.8 | 3.5 | 3.3 | 3.1 | 1.7 | 2.5 | 2.4 | 2.2 |

INDUSTRIAL APPLICABILITY

By the method for dimerizing butenes of the present invention, an octene mixture having a low degree of branching can be produced economically in a high yield, and alcohols produced by using the octenes show a comprehensively excellent performance as a raw material of a plasticizer and are of great value in industrial use.

We claim:

1. A method for dimerizing butenes in the presence of a catalyst, wherein a catalyst system is used which is produced in situ from (i) an organonickel compound having no nickel-halogen bond, (ii) a triarylphosphine and/or a monoalkyldiarylphosphine, (iii) an organoaluminum compound and (iv) hydrogen.

2. The method for dimerizing butenes according to claim 1, wherein the organonickel compound having no nickel-halogen bond is a carboxylic acid salt of nickel.

3. The method for dimerizing butenes according to claim 1, wherein the organonickel compound having no nickel-halogen bond is a complex compound of nickel having no inorganic radical.

4. The method for dimerizing butenes according to claim 1, wherein the organoaluminum compound is an alkylaluminum halide compound.

5. The method for dimerizing butenes according to claim 1, wherein the triarylphosphine is a compound of the general formula $PAr_3$ (wherein Ar is a phenyl group or a naphthyl group which may have a substituent, and said substituent is a hydrocarbon group, an alkoxy group or a halogen atom).

6. The method for dimerizing butenes according to claim 1, wherein the triarylphosphine is triphenylphosphine.

7. The method for dimerizing butenes according to claim 1, wherein the triarylphosphine is a tris(p-substituted phenyl)phosphine.

8. The method for dimerizing butenes according to claim 1, wherein the monoalkyldiarylphosphine is a compound of the general formula $PRAr_2$ (wherein Ar is a phenyl group or a naphthyl group which may have a substituent, said substituent is a hydrocarbon group, an alkoxy group or a halogen atom, and R is an alkyl group having from 1 to 8 carbon atoms).

9. The method for dimerizing butenes according to claim 1, wherein a mixture or a complex of the organonickel compound having no nickel-halogen bond and the triarylphosphine or the monoalkyldiarylphosphine compound is brought into contact with the organoaluminum compound in the presence of butenes simultaneously.

10. The method for dimerizing butenes according to claim 1, wherein the molar ratio of the organoaluminum compound to the organonickel compound having no nickel-halogen bond is within a range of from 2 to 100.

11. The method for dimerizing butenes according to claim 1, wherein a molar ratio of the triarylphosphine and/or the monoalkyldiarylphosphine compound to the organonickel compound is from 0.5 to 5.

12. A dimeric composition of butenes which is a high-molecular weight product obtained by dimerization of butenes, wherein the content of octenes is at least 70% by weight, the total of the contents of normal octene, monomethylheptene and dimethylhexene in the octenes is at least 90% by weight, the content of highly-branched forms which are branched not less than dimethylhexene in the octenes is at most 15% by weight and the average degree of branching of the octenes is from 0.85 to 1.15.

13. A method for producing alcohols wherein a product obtained by dimerization of butenes in the presence of a catalytic system produced in situ from (i) an organonickel compound having no nickel-halogen bond, (ii) a triarylphosphine and/or a monoalkyldiarylphosphine, (iii) an organoaluminum compound and (iv) hydrogen is subjected to a hydroformylation reaction and a hydrogenation reaction.

14. The method for producing alcohols according to claim 13, wherein a Rh catalyst is used in the hydroformylation reaction.

15. The method for producing alcohols according to claim 13, wherein a Co catalyst is used in the hydroformylation reaction.

16. A method for producing alcohols wherein a dimeric composition of butenes in which the content of octenes is at least 70% by weight, the total of the contents of normal octene, monomethylheptene and dimethylhexene in the octenes is at least 90% by weight, the content of highly-branched forms which are branched not less than dimethylhexene is at most 15% by weight and the average degree of branching of the octenes is from 0.85 to 1.15, is subjected to a hydroformylation reaction and a hydrogenation reaction.

17. The method for producing alcohols according to claim 16, wherein a Rh catalyst is used in the hydroformylation reaction.

18. The method for producing alcohols according to claim 16, wherein a Co catalyst is used in the hydroformylation reaction.

* * * * *